(12) United States Patent
Quiñones et al.

(10) Patent No.: US 11,371,073 B2
(45) Date of Patent: Jun. 28, 2022

(54) LISTERIA DETECTION

(71) Applicant: The United States of America, as Represented by the Secretary of Agriculture, Washington, DC (US)

(72) Inventors: Beatriz Quiñones, San Pablo, CA (US); Bertram G. Lee, San Francisco, CA (US); Jaszemyn C. Yambao, Fairfield, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/815,323

(22) Filed: Mar. 11, 2020

(65) Prior Publication Data

US 2021/0285023 A1    Sep. 16, 2021

(51) Int. Cl.
*C12Q 1/6853*    (2018.01)
*C12Q 1/686*    (2018.01)
*C12Q 1/04*    (2006.01)

(52) U.S. Cl.
CPC ............ *C12Q 1/04* (2013.01); *C12Q 1/686* (2013.01); *C12Q 1/6853* (2013.01); *C12Q 2561/113* (2013.01)

(58) Field of Classification Search
None
See application file for complete search history.

(56) References Cited

U.S. PATENT DOCUMENTS

| | | |
|---|---|---|
| 5,139,933 A | 8/1992 | Green et al. |
| 5,491,068 A | 2/1996 | Benjamin et al. |
| 5,695,946 A | 12/1997 | Benjamin et al. |
| 8,748,133 B2 | 6/2014 | Reshatoff et al. |
| 8,795,969 B2 | 8/2014 | Petrauskene et al. |
| 9,273,340 B2 | 3/2016 | Moriyama et al. |
| 9,546,405 B2 | 1/2017 | Petrauskene et al. |
| 9,593,383 B2 | 3/2017 | Reshatoff et al. |
| 9,719,124 B2 | 8/2017 | Moriyama et al. |
| 10,501,812 B2 | 12/2019 | Reshatoff et al. |

FOREIGN PATENT DOCUMENTS

CN    103667251 A    *    3/2014

OTHER PUBLICATIONS

GenBank Accession No. CP055232.1 [retrieved on-line, retrieval date: Sep. 8, 2021, retrieved from: https://www.ncbi.nlm.nih.gov/nuccore/CP055232.1] (Year: 2021).*
GenBank Accession No. MZ948955.1 [retrieved on-line, retrieval date: Sep. 8, 2021, retrieved from: https://www.ncbi.nlm.nih.gov/nuccore/MZ948955.1] (Year: 2021).*
GenBank Accession No. MZ675515.1 [retrieved on-line, retrieval date: Sep. 8, 2021, retrieved from: https://www.ncbi.nlm.nih.gov/nuccore/MZ675515.1] (Year: 2021).*
Google translation of CN-103667251-A1 (translated on Sep. 8, 2021, from: https://patentimages.storage.googleapis.com/ae/9f/de/61e9f5beefcaf8/CN103667251A.pdf) (Year: 2014).*
Bassler et al., "Use of a Fluorogenic Probe in a PCR-Based Assay for the Detection of Listeria monocytogenes," Applied and Environmental Microbiology, October, vol. 61, No. 10, pp. 3724-3728. (Year: 1995).*
Feng et al., "Detection of Listeria monocytogenes based on a combined aptamers magnetic capture and loop-mediated isothermal amplification," Food Control, vol. 85, print out pp. 1-25 (Year: 2018).*
Brouillette R. et al., 2014, "Listeria monocytogenes guidance on environmental monitoring and corrective actions in at-risk foods," Washington, D.C. Grocery Manufacturers Association pp. 1-35.
Glaser P. et al., 2001, "Comparative genomics of Listeria species," Science 294: 849-852.
Kaplan R.M., et al., 2014, "Big data and large sample size: A cautionary note on the potential for bias," J. Clin. Transl. Sci. 7: 342-346.
Kuiper H.A. and Paoletti C., 2015, "Food and feed safety assessment: The importance of proper sampling," J. AOAC Int. 98: 252-258.
Kutyavin I.V., 2008, "Use of base-modified duplex-stabilizing deoxynucleoside 5'-triphosphates to enhance the hybridization properties of primers and probes in detection polymerase chain reaction," Biochemistry 47: 13666-13673.
Livezey K. et al., 2013, "A new generation of food-borne pathogen detection based on ribosomal RNA," Annu. Rev. Food Sci. Technol. 4: 313-325.
Milner M.G., et al., 2001, "Relationship between nucleic acid ratios and growth in Listeria monocytogenes," Microbiology 147: 2689-2696.
Murakami, T., 2012, "Filter-based pathogen enrichment technology for detection of multiple viable foodborne pathogens in 1 day," J. Food Prot. 75: 1603-1610.
Orsi R.H. and Weidmann M., 2016, "Characteristics and distribution of *Listeria* spp., including Listeria species newly described since 2009," Appl Microbiol Biotechnol 100: 5273-5287.
Philpott C., 2009, "A summary profile of pathogen detection technologies," In Food Safety Magazine, Glendale, California, USA.
Reddington K., et al., (2014), "A current overview of commercially available nucleic acid diagnostics approaches to detect and identify human gastroenteritis pathogens," Biomol Detect Quantif, 1:3-7.
Suh S.H., et al., 2014, "Nucleic acid aptamers for capture and detection of *Listeria* spp.," Anal. Biochem. 459:39-45.

(Continued)

*Primary Examiner* — Young J Kim
(74) *Attorney, Agent, or Firm* — Maria Restrepo-Hartwig; John D. Fado

(57) ABSTRACT

Provided are compositions, kits, and methods for the accurate detection of *Listeria*. In certain aspects and embodiments, the compositions, kits, and methods may provide improvements in relation to specificity, sensitivity, and speed of detection.

9 Claims, 8 Drawing Sheets
Specification includes a Sequence Listing.

(56) References Cited

OTHER PUBLICATIONS

The United Fresh Food Safety & Technology Council, 2018, "Guidance on environmental monitoring and control of Listeria for the fresh produce industry," Washington, D.C.: United Fresh Produce Association, pp. 1-65.

Zoellner, C., et al., 2018, "Design elements of Listeria environmental monitoring programs in food processing facilities: A scoping review of research and guidance materials," Compr. Rev. Food Sci. Food Saf. 17:1156-1171.

\* cited by examiner

LISTERIA DETECTION

Disclosed herein are compositions, kits, and methods used for the detection of *Listeria*.

SEQUENCE LISTING

The instant application contains a Sequence Listing which has been submitted via EFS-Web as ASCII compliant text file format (.txt), and is hereby incorporated by reference in its entirety. The ASCII file was created on Mar. 11, 2020, is named SequenceListing, and has 5 kilobytes. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

*Listeria* are gram-positive bacteria found in soil and water. Vegetables can become contaminated with *Listeria* from contact with contaminated soil, animals, humans, or manure used as fertilizer. Animals can carry the bacterium without appearing ill and can contaminate foods of animal origin such as meats and dairy products. Listeriosis, a serious infection caused by eating food contaminated with the bacterium *Listeria monocytogenes* (*L. monocytogenes*), has been recognized as an important public health problem in the United States and is a leading cause of death due to foodborne illness. In the United States alone, there has been an estimated 1,500 listeriosis cases each year, and of those, approximately 300 cases have resulted in death. Persons with an increased risk of listeriosis are pregnant women, newborns, the elderly, individuals with a weakened immune system, individuals who take glucocorticoid medications, as well as patients suffering from cancer, diabetes, kidney disease, or AIDS. In addition to *L. monocytogenes*, other *Listeria* species include *Listeria innocua*, *Listeria welshimeri*, *Listeria ivanovii*, *Listeria seeligeri*, *Listeria grayi*, and *Listeria murrayi* (Orsi R. H. and Weidmann M., 2016, "Characteristics and distribution of *Listeria* spp., including *Listeria* species newly described since 2009," Appl Microbiol Biotechnol 100: 5273-5287)

*L. monocytogenes* is a significant cause of foodborne illness. In the general population, most cases of foodborne illnesses are expressed as a mild illness, but susceptible populations of pregnant women, neonates, elderly, or immunocompromised humans have a much higher incidence of systemic listeriosis with an approximate 20-30% mortality rate. Recently, high profile outbreaks of *L. monocytogenes* have been associated with fresh produce and ready-to eat foods. The annual economic impact of listeriosis in the United States alone is estimated at over US$2.8 billion. *L. monocytogenes* is widespread in the environment; therefore, food production facilities constantly monitor and control for the presence of *Listeria* species on surfaces. *Listeria* species are considered a broad indicator of the conditions potentially favorable for *L. monocytogenes* growth and survival in the environment (Brouillette R. et al., 2014, "*Listeria monocytogenes* guidance on environmental monitoring and corrective actions in at-risk foods," Washington, D.C. Grocery Manufacturers Association pp. 1-35; The United Fresh Food Safety & Technology Council, 2018, "Guidance on environmental monitoring and control of *Listeria* for the fresh produce industry," Washington, D.C.: United Fresh Produce Association. pp. 1-65; Zoellner, C., et al., 2018, "Design elements of *Listeria* environmental monitoring programs in food processing facilities: A scoping review of research and guidance materials," Compr. Rev. Food Sci. Food Saf. 17: 1156-1171).

The food industry typically holds finished product in storage for three days or more while waiting for pathogen test results. For food processors, rapid testing will significantly reduce the time required to react to an order, the quantity and variety of inventory needed to be carried, and the amount of waste due to spoilage (Philpott, C., 2009, "A summary profile of pathogen detection technologies," in Food Safety Magazine, Glendale, Calif., USA).

U.S. Pat. No. 5,139,933 discloses a method for quickly detecting the presence of *Listeria* in samples by using antibodies to selectively capture the peptidoglycan and teichoic acid components of the listeriae bacterial cell wall.

U.S. Pat. Nos. 5,491,068 and 5,695,946 disclose a method for detecting organisms capable of being cultured, such as bacteria, by capturing the bacterial cells using specialized magnetic beads; incubating the captured cells to form colonies; removing material from the colonies with a colony lift membrane; and detecting the colony material on the membrane sheet by use of labeled antibodies, PCR, or nucleic acid probes.

U.S. Pat. Nos. 9,273,340 and 9,719,124 disclose a method for detecting *L. monocytogenes*. The method comprises providing a culture device with a selective culture medium and a detection article comprising a first indicator system. The selective culture medium facilitates the growth of *Listeria* microorganisms. When a *Listeria* microorganism is detected in a sample contacted with the culture medium, the detection article is contacted with the culture medium to detect *L. monocytogenes*.

U.S. Pat. Nos. 8,795,969 and 9,546,405 disclose methods for detecting *Listeria* species by amplification using primers and probe sets with similarity to the *L. monocytogenes* rnpB gene. The claims recite specific probe and primer sequences.

U.S. Pat. Nos. 8,748,133; 9,593,383; and 10,501,812 disclose compositions, kits, and methods used for monitoring environmental surfaces for *Listeria* species. U.S. Pat. No. 10,501,812 claims a method for detecting *Listeria* in a sample by performing nucleic acid amplification using oligonucleotides comprising a T7 provider oligonucleotide and a primer oligonucleotide. The T7 provider oligonucleotide and the primer oligonucleotide target *Listeria* sequences corresponding to nucleotides 1180 to 1370 of the *Escherichia coli* 16S rRNA. U.S. Pat. No. 8,748,133 claims a method for detecting *Listeria* in a sample by performing a nucleic acid amplification using a set of oligonucleotides comprising two or more T7 provider oligonucleotides and one or more primer oligonucleotides. Where the T7 provider oligonucleotides and the primer oligonucleotide amplify nucleic acids from *L. monocytogenes*, *L. innocua*, *L. grayi*, *L. ivanovii*, *L. welshimeri*, *L. murrayi*, and *L. seeligeri* without substantial amplification of nucleic acid from *Brochothrix thermosphacta* or *Erysipelothrix rhusiopathiae*. At least one of the T7 provider oligonucleotides targets a sequence corresponding to specific *Listeria* nucleotide positions. U.S. Pat. No. 9,593,383 claims a method for detecting *Listeria* in a sample by performing a nucleic acid amplification assay using a set of oligonucleotides comprising a T7 provider oligonucleotide and a primer oligonucleotide. The T7 provider oligonucleotide and the primer oligonucleotide have specific nucleic acid sequences.

Thus, there is a need for a rapid and sensitive method for specifically detecting low cell concentrations of *Listeria* species from environmental samples.

SUMMARY OF THE INVENTION

The inventors have devised novel compositions, kits, and methods for the detection of *Listeria* species.

In an embodiment, the invention relates to a bacteria detection kit comprising at least one oligonucleotide that specifically binds to the bacteria. In some embodiments of the invention, at least one oligonucleotide that specifically binds to the bacteria in the bacteria detection kit is a forward primer, a reverse primer, a probe, an aptamer, a spacer sequence for aptamer extension, or a tether sequence for aptamer surface attachment. In some embodiments of the invention, the bacteria detection kit comprises a forward primer, a reverse primer, a probe, an aptamer, a spacer sequence for aptamer extension, and a tether sequence for aptamer surface attachment. In some embodiments of the invention, the tether sequence for aptamer surface attachment in the kit of the invention binds to a capture column. In some embodiments of the invention, at least one oligonucleotide that specifically binds to the bacteria in the bacteria detection kit has the nucleic acid sequence set forth in SEQ ID NO: 1; SEQ ID NO: 2; SEQ ID NO: 3; SEQ ID NO: 4; SEQ ID NO: 5; SEQ ID NO: 6; or SEQ ID NO: 7. In some embodiments of the invention, the bacteria detection kit comprising at least one oligonucleotide that specifically binds to the bacterial nucleic acids further comprises polynucleotide-amplification reagents. In some embodiments of the invention, the bacteria detected by the detection kit of the invention is *Listeria*.

In an embodiment, the invention relates to a method for detecting *Listeria* in a sample. The method comprises capturing bacterial cells in the sample by using aptamers; lysing the captured bacterial cells; and amplifying bacterial polynucleotides; where the presence of amplified polynucleotides is an indication that *Listeria* is present in the sample. In some embodiments, in the method for detecting *Listeria* in a sample, at least one of the steps for capturing and lysing of the bacterial cells is performed inside a temperature-controlled chamber. In some embodiments of the invention, in the method for detecting *Listeria* in a sample, both the capturing and the lysing of the bacterial cells is performed inside a temperature-controlled chamber. In some embodiments of the invention, in the method for detecting *Listeria* in a sample, the bacterial cells are captured using aptamers. In some embodiments of the invention, the bacterial polynucleotides amplified in the method for detecting *Listeria* in a sample are RNA. In some embodiments of the invention, the bacterial polynucleotides amplified in the method for detecting *Listeria* in a sample are amplified using quantitative reverse transcription polymerase chain reaction (qRT-PCR). In some embodiments of the invention, the sample in the method for detecting *Listeria* in a sample is an environmental sample. In some embodiments of the invention, in the method for detecting *Listeria* in a sample, the bacterial cells are captured using at least one aptamer.

In some embodiments of the invention, in the method for detecting *Listeria* in a sample, at least one aptamer binds to a spacer sequence. In some embodiments of the invention, in the method for detecting *Listeria* in a sample, the aptamer is modified with a spacer sequence, which then binds to a tether sequence for surface attachment. In some embodiments of the invention, in the method for detecting *Listeria* in a sample, at least one aptamer has the sequence set forth in SEQ ID NO: 6, the spacer sequence for aptamer extension has the sequence set forth in SEQ ID NO: 5; and the tether sequence for aptamer surface attachment has the sequence set forth in SEQ ID NO: 4. In some embodiments of the invention, in the method for detecting *Listeria* in a sample, the sequences of the oligonucleotides used for qRT-PCR amplification are set forth in SEQ ID NO: 1; SEQ ID NO: 2; and SEQ ID NO: 3.

In an embodiment, the invention is related to a *Listeria*-specific oligonucleotide designed by aligning RNA ribosome sequences from at least one hundred genomes of *Listeria* and non-targeted bacterial species; selecting regions in the RNA ribosomal sequences with the most heterogeneity between the *Listeria* sequences and the non-targeted sequences; performing simulated folding of the selected RNA regions to assess accessibility of the detected RNA region; and its duplex stabilizing technology, GC content, annealing temperatures, and self-hybridization information to select the best candidates for *Listeria*-specific oligonucleotides.

BRIEF DESCRIPTION OF THE DRAWINGS

FIG. 2A depicts a representation of an aptamer [14] (set forth in SEQ ID NO: 6), modified with a spacer sequence for aptamer extension [15] (set forth in SEQ ID NO: 5), bound on a surface [17] by the tether sequence for aptamer surface attachment [16] (set forth in SEQ ID NO: 4). FIG. 2B depicts a representation of the forward primer BH1-F; reverse primer BH1-R; and probe BH1-P bound to *Listeria* DNA (SEQ ID NO: 7). The position on the chromosome of the *Listeria* DNA is indicated above the primers and probe. The nucleotide positions in the aptamer and the *Listeria* DNA sequences are indicated at every $10^{th}$ nucleotide.

BRIEF DESCRIPTION OF THE SEQUENCES

The oligonucleotide sequences used in the instant disclosure, and their corresponding sequence identifiers are listed below in Table 1.

| Name | Oligonucleotide sequence | SEQ ID NO: |
|---|---|---|
| Forward primer | 5'-CCTTACCAGGTCTTGACATTCTTTG-3' | 1 |
| Reverse primer | 5'-GAGCTGACGACAACCATGC-3' | 2 |
| Detection probe | 5'- CACTCTGGAGACAGAGCTTT -3' | 3 |
| Tether sequence | 5'-CAACTTTCAAAACAAAAACTTTTTTTTT-Amino C6-3' | 4 |
| Spacer sequence | 5'-GTTTTTGTTTTGAAAGTTGTTTTTTTTTT-3' | 5 |
| Aptamer | 5'-AGTATACGTATTACCTGCAGCTCTGTGTTCCGTTTTCGATTCTTACTGTGTTTTCGGGTGCCGATATCTCGGAGATCTTGC-3' | 6 |
| *Listeria monocytogenes* DNA | 5'-CCTTACCAGGTCTTGACATCCTTTGACCACTCTGGAGACAGAGCTTTCCCTTCGGGGACAAAGTGACAGGTGGTGCATGGTTGTCGTCAGCTC-3' | 7 |

DETAILED DESCRIPTION

The inventors have developed and refined compositions, kits, and methods for a rapid assay to effectively determine the presence of *Listeria* cells.

The bacterial foodborne pathogen, *L. monocytogenes*, has been significantly implicated in high-profile outbreaks linked to fresh produce. The annual economic impact of listeriosis in the United States alone is estimated at over US$2.8 billion. The inventors have collaborated with the agricultural technology sector to develop and validate a flow-through system as an integrated detection platform for the in-process surveillance of foodborne pathogens. To achieve a high level of sensitivity in environmental samples, the method targeted conserved high copy sequences in the ribosomal RNA of *Listeria* species (Millner, M. G., et al. 2001, "Relationship between nucleic acid ratios and growth in *Listeria monocytogenes*," Microbiology 147: 2689-2696). Bacterial cells were subjected to an aptamer-capture step, followed by sample concentration, and mechanical lysis. Some RNA copies were purified, and some were recovered from crude lysates prior to amplification using reverse transcription. Amplification of the ribosomal RNA target region was achieved by using modified nucleotides to stabilize probe-target DNA duplex, and to promote higher specificity of probe.

Figure 1:
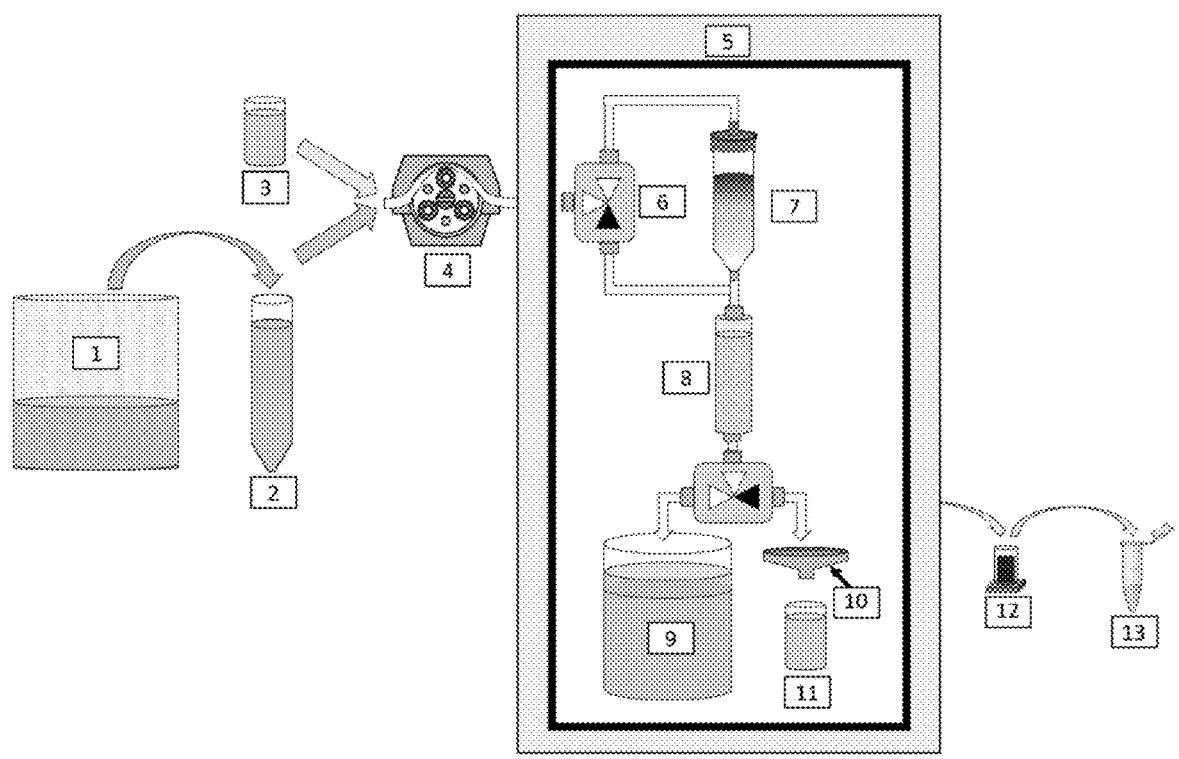
FIG. 1 depicts a schematic diagram of the *Listeria* sampling processing steps in a flow through system as part of the invention. Sample is blended with PBS in container [1]; blended sample is filtered to remove large soil particulates into sample container [2]; buffer [3] is added to sample and a pump [4], introduces the liquid into temperature-controlled chamber [5]. Microfluidic valves [6] move homogenized sample to a depth filter [7] and *Listeria* cells in the sample are sequestered with an aptamer capture column [8]. Potential inhibitors are removed as waste [9], the cells are subjected to mechanical lysis and [10], and further collected [11]. The lysed cells can be transferred to an RNA extraction system for purification [12], and the RNA (either in the crude lysate or purified) is subjected to further amplification by qRT-PCR [13].

The inventors have developed a method for testing environmental swab samples for the presence of *Listeria*. A schematic diagram of the sampling, processing steps, and *Listeria* detection methods of the invention are depicted in FIG. 1. Briefly, environmental swab samples were obtained and homogenized with phosphate buffered saline (PBS) in a filter bag [1]; the blended sample was transferred into sample container [2]; the filtered sample was combined with buffers [3] using pump [4]; and the homogenized material was introduced into a temperature controlled chamber [5]. In the temperature controlled chamber [5]; a microfluidic valve [6] moved the homogenized sample to a depth filter [7] to remove larger and unwanted particles and inhibitors; the filtered material entered a column [8] where bacterial cells in the sample were captured using aptamers; and additional potential inhibitors and excess volume were removed as waste [9]; the captured bacterial cells were subjected to mechanical lysis [10] and further collected in concentrated volumes [11]; and the lysed cells were subsequently transferred and collected outside of the temperature controlled chamber [5] to an RNA extraction system [12]. The RNA was then subjected to amplification [13].

Figure 2A:
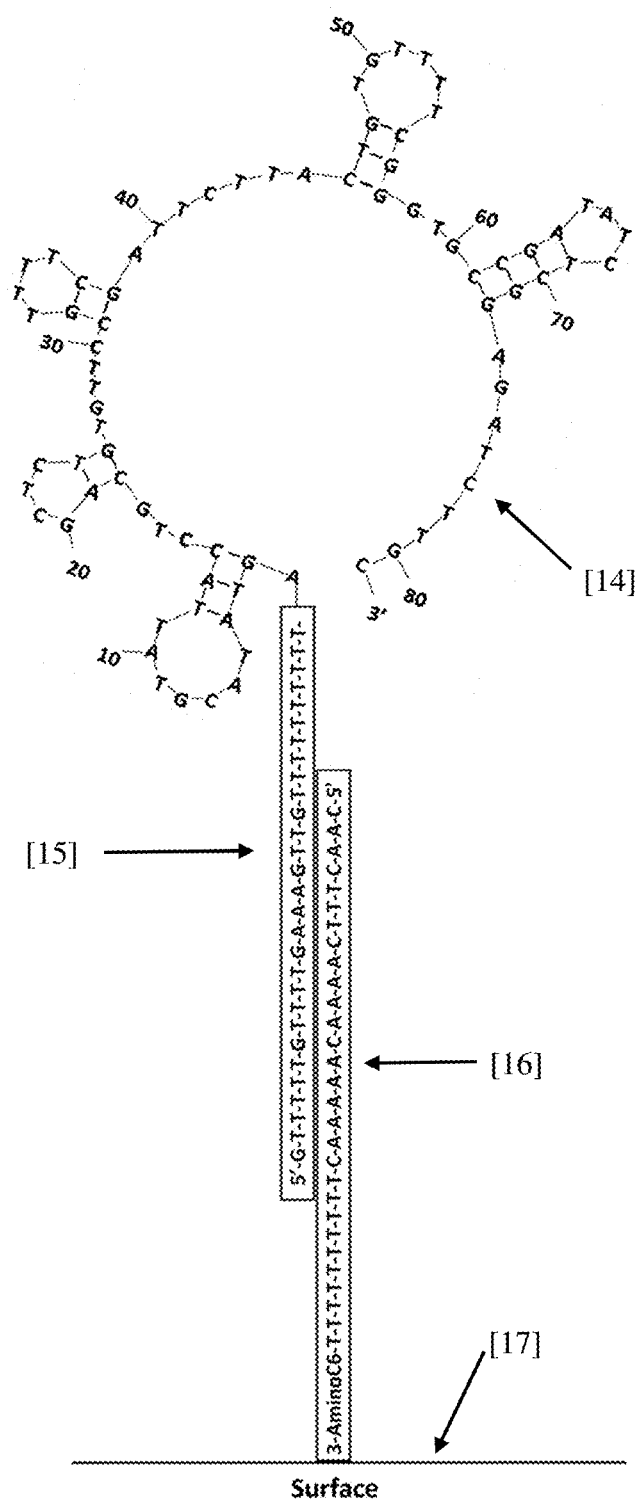
FIG. 2A and FIG. 2B depict the aptamer and primer sequences of the invention and their association with the methods in the application.
Figure 2B:
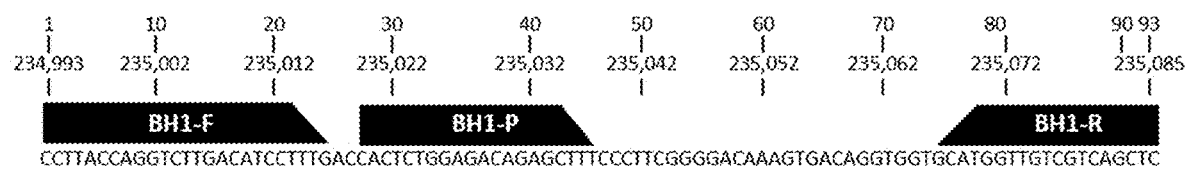

Aptamers were modified with an oligonucleotide serving as spacer sequence for aptamer extension, and were attached to the surface of the capture column [8] by another oligonucleotide serving as tether sequence for aptamer surface attachment. FIG. 2A shows the aptamer sequence (set forth in SEQ ID NO: 6) modified with the spacer sequence for aptamer extension (set forth in SEQ ID NO: 5), which is annealing to the tether sequence for aptamer surface attachment (set forth in SEQ ID NO: 4), which is then bound to the surface of the capture column. The tether sequence for aptamer surface attachment has an Amino C6 linker at the 3' end of the nucleotide sequence to enable binding to the capture column surface. The spacer and tether sequences were designed to allow optimal orientation of the aptamer to capture the *Listeria* target cells and enable the aptamers to be released from the column for further downstream processing. The aptamer-captured *Listeria* cells were mechanically lysed in molecular biology-grade water. After extraction, *Listeria* RNA was amplified and detected with a qRT-PCR reaction using forward primer BH1-F, reverse primer BH1-R, and probe BH1-P. FIG. 2B depicts binding of primer BH1-F (set forth in SEQ ID NO: 1), primer BH1-R (set forth in SEQ ID NO:2), and probe BH1-P (set forth in SEQ ID NO:3) bound to *Listeria* DNA sequence (set forth in SEQ ID NO: 7).

Figure 3:
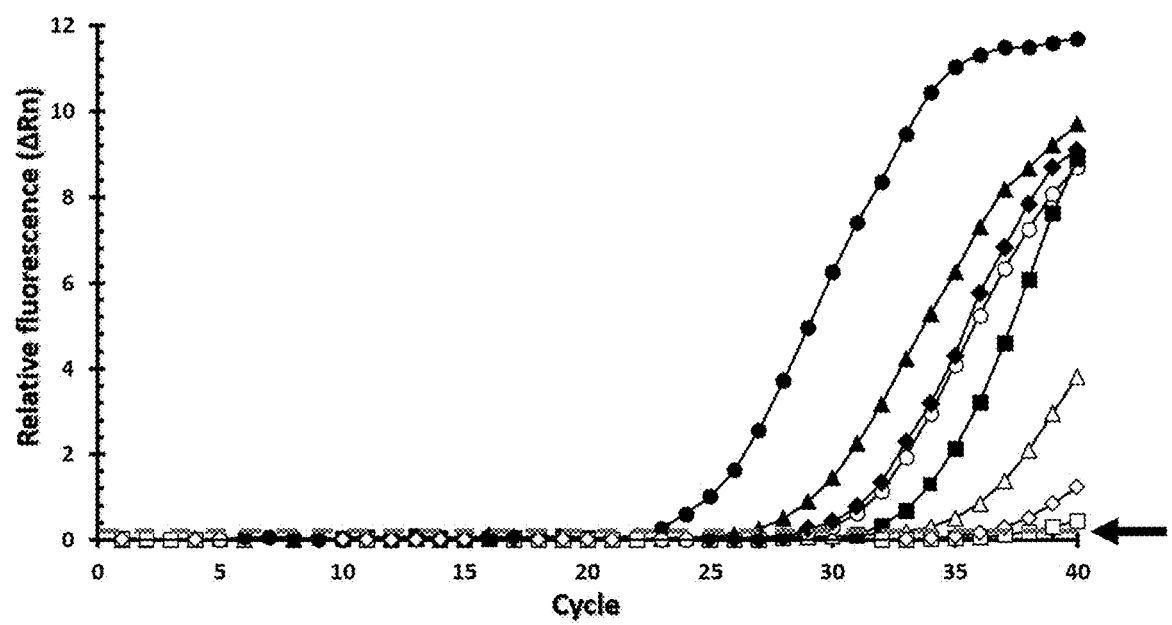
FIG. 3 depicts a graph of the relative fluorescence as a function of amplification cycles. The Y-axis shows the relative fluorescence ($\Delta$Rn), the X-axis shows the number of amplification cycles. Filled symbols represent data obtained with the RNA-based assay of the invention; open symbols represent data obtained with the commercially available MICROSEQ *Listeria monocytogenes* detection kit. Circles represent data for approximately 5,000 bacterial cells, triangles represent data for approximately 500 bacterial cells, diamonds represent data for approximately 50 bacterial cells, and squares represent data for approximately 5 bacterial cells. The detection threshold is indicated by an arrow to the right of the graph.

Validation experiments indicated that the assay taught here had an RNA analytical sensitivity limit of less than 10 fg of *Listeria* RNA. This number is less than 5 CFU/mL when using crude lysate as template (Fisher's exact test, $p<0.0001$). As shown in FIG. 3, the RNA-based assay (filled symbols) of the instant invention was found to be about 100-times more sensitive than the DNA-based commercial kit (open symbols).

Figure 4:
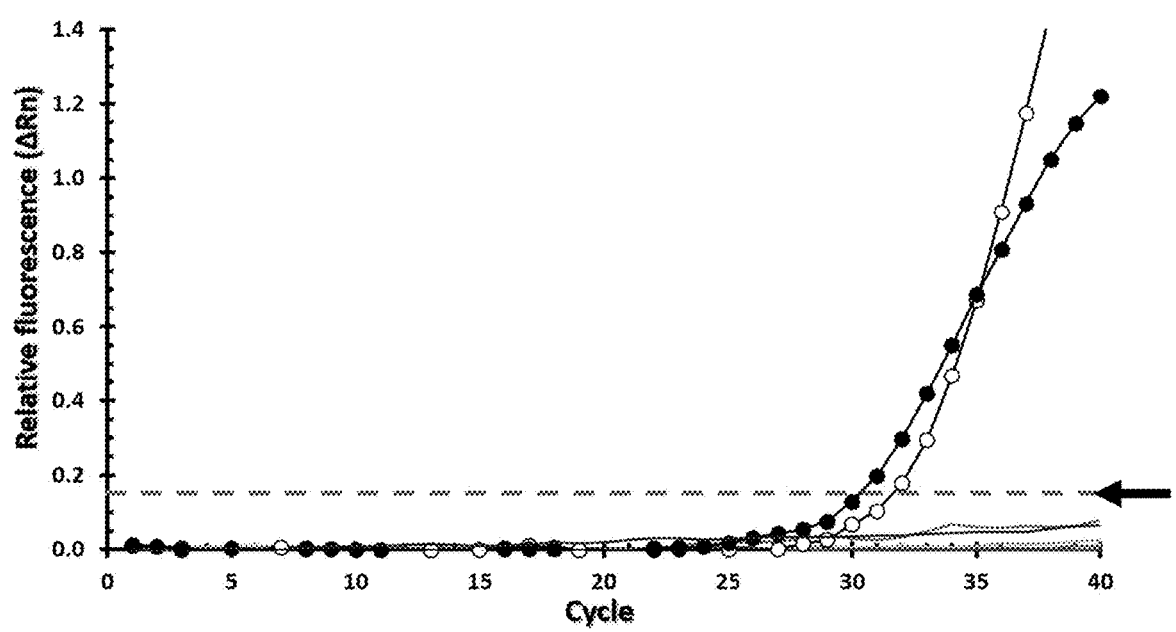
FIG. 4 depicts a graph of the relative fluorescence as a function of the number of amplification cycles using the assay taught herein. The Y-axis shows the relative fluorescence ($\Delta$Rn), the X-axis shows the number of amplification cycles. Filled circles represent data obtained for *L. monocytogenes* strain RM2199 and open circles represent data obtained for *Listeria grayi* strain RM2208. Data obtained for the negative control and for other gram-positive or gram-negative bacteria is presented with lines without symbols. The detection threshold is indicated by an arrow to the right of the graph.
Figure 5:
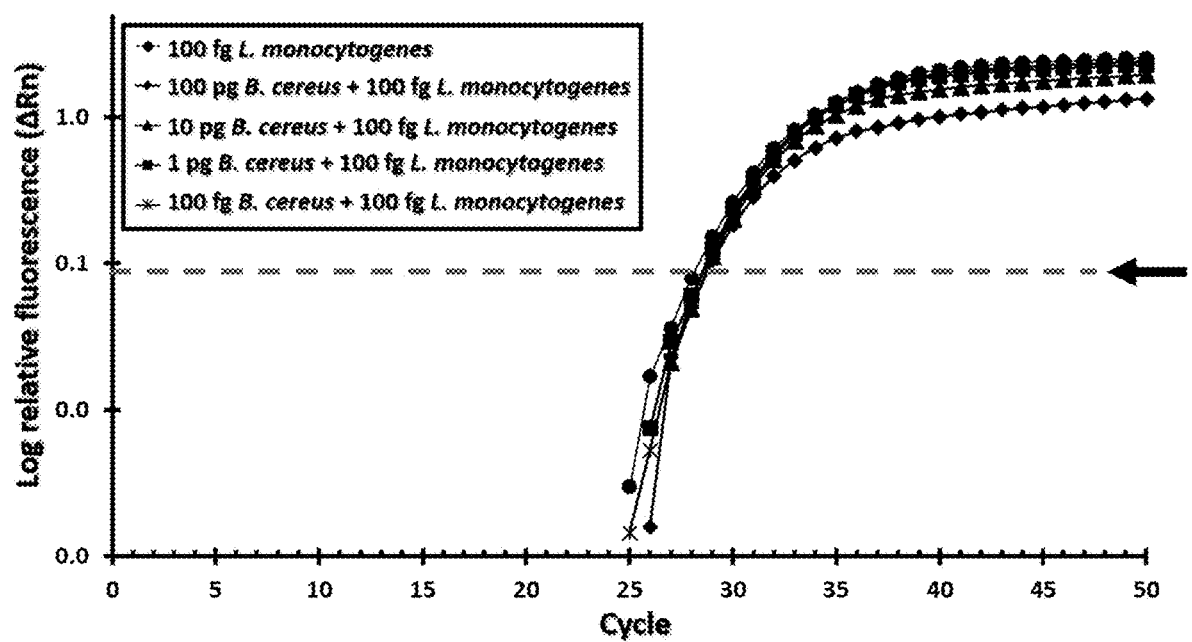
FIG. 5 depicts a graph of the relative amounts of *L. monocytogenes* detected in the presence of excess non-target RNA from *Bacillus cereus*. The Y-axis shows the relative fluorescence (ΔRn), the X-axis shows the number of PCR cycles. Filled circles represent data for 100 fg *L. monocytogenes*; filled diamonds represent data for 100 fg *L. monocytogenes* plus 100 pg *B. cereus*; filled triangles represent data for 100 fg *L. monocytogenes* plus 10 pg *B. cereus*; filled squares represent data for 100 fg *L. monocytogenes* plus 10 pg *B. cereus*; asterisks represent data for 100 fg *L. monocytogenes* plus 100 fg *B. cereus*. The detection threshold is indicated by an arrow and a dashed line.
Figure 6:
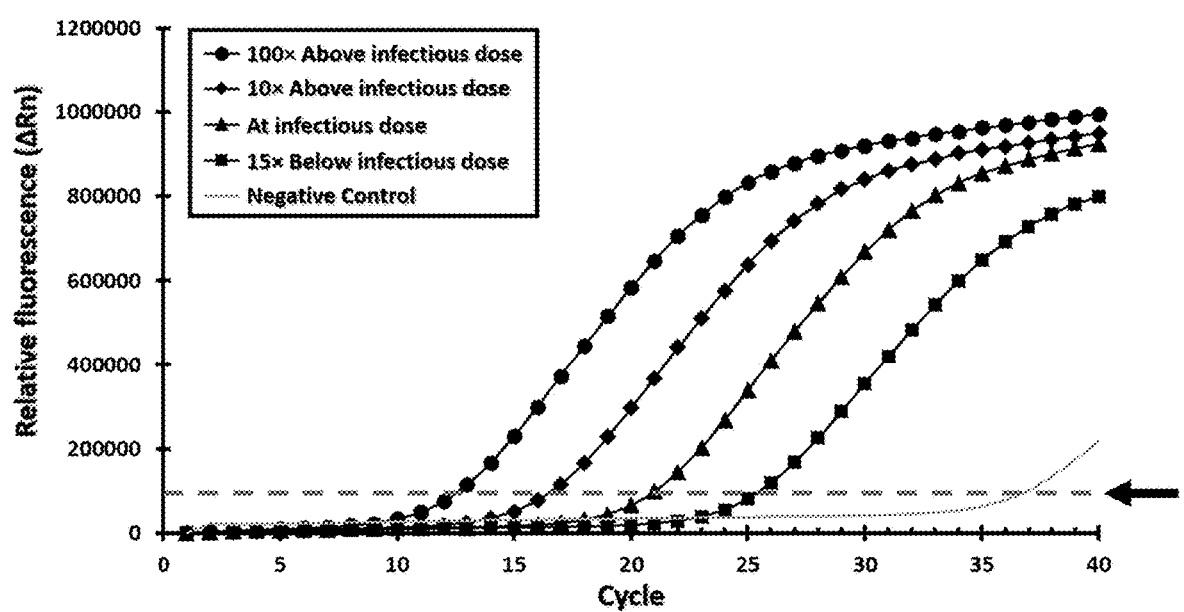
FIG. 6 depicts a graph of the detection sensitivity of the assay taught herein. The Y-axis shows the relative fluorescence (ΔRn), the X-axis shows the number of amplification cycles. Filled circles present data for sample with *Listeria* 100 times above infectious dose; filled diamonds present data for sample with *Listeria* 10 times above infectious dose; filled triangles present data for *Listeria* at infectious dose; filled squares present data for *Listeria* 15 times below infectious dose; negative control line has no additional symbols. The detection threshold is indicated by an arrow to the right of the graph.

No positive signals were detected when testing non-targeted environmental bacterial species belonging to *Bacillus, Citrobacter, Enterobacter*, and *Pseudomonas*. Preliminary observations indicated that low concentrations of *Listeria* were detected even in the presence of 1000 times the amount of RNA from non-targeted bacterial species. Using the assay of the invention, high and specific fluorescent signals were recorded when examining the targeted either the clinical *L. monocytogenes* strain RM2199 or the plant-associated *L. grayi* strain RM2208, while no signal amplification was detected for any of the tested non-target strains. As seen in Table 2 (below) and in FIG. 4, the only specific positive signal was obtained from *L. monocytogenes* and *L. grayi*. The dashed line and the arrow in FIG. 4 indicate the detection threshold limit of the assay. No amplification (CT value) was detected for any of the non-targeted bacterial strains tested. As seen in FIG. 5, the assay of the invention detected low amounts of *L. monocytogenes*, even in the presence of excess RNA in various amounts from the non-targeted *B. cereus* strain ATCC 14579. As seen in FIG. 6, the negative control samples amplified below the detection threshold limit, and the Ct-values of the serial dilutions were about four cycles apart. This data indicates that the amplification of target *Listeria* RNA sequences are close to 100% efficiency when using the BH1-F and BH1-R primers, and BH1-P probe. The improved mechanical lysis employed in this detection method also resulted in a detection sensitivity below the infectious dose of *L. monocytogenes*.

Figure 7:
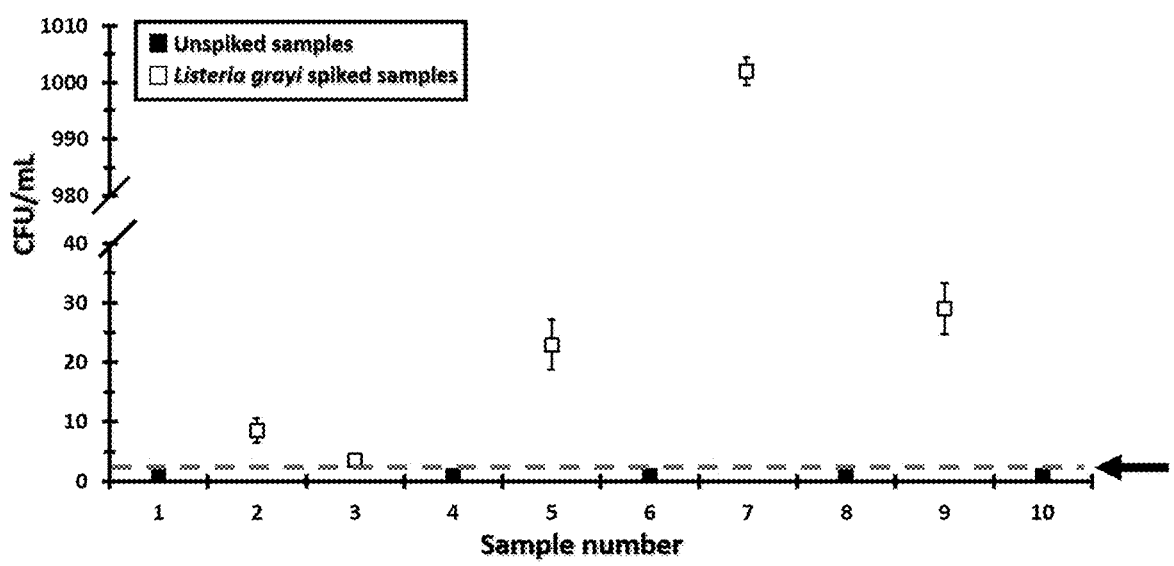
FIG. 7 depicts a graph of the *Listeria* cell forming units measured in a blind test of environmental swab samples subjected to the aptamer capture test after being either spiked or not spiked with *Listeria*. The Y-axis shows the *Listeria* CFU/mL, the X-axis shows the sample numbers. Samples 1, 4, 6, 8, and 10 were not spiked with *Listeria*, while samples 2, 3, 5, 7, and 9 were spiked with *Listeria*. The detection threshold is indicated by an arrow to the right of the graph.

The feasibility of employing the aptamer capture step for detecting *Listeria* species from sponge-swab samples collected at a leafy greens processing facility was evaluated. The aptamer-based capture test accurately detected *Listeria* species in a blind test of environmental swab samples, some of which were spiked with *L. grayi*. As seen in FIG. 7, the assay of the invention accurately detected *Listeria* in all spiked samples, while no positive signal was recorded in any of the samples that were not spiked with *Listeria*, indicating that the assay did not report false positive or false negative results. The amount of bacteria detected in the unspiked samples was below 1 CFU/mL, and below the threshold limit of detection of the assay. Thus, preliminary results showed that *Listeria* species were accurately detected in the environmental swab samples at concentrations ranging from 3 CFU/mL to 32 CFU/mL (Fisher's exact test, $p<0.001$), which were recovered from 100 mL-volume samples spiked with *Listeria* in the absence of an enrichment culturing step.

In certain aspects and embodiments, the invention relates to compositions, methods, and kits for the identification, detection, and/or quantitation of *Listeria*, which may be present either alone or as a component, large or small, of a homogeneous or heterogeneous mixture of nucleic acids in a sample. The sample may be taken for diagnostic testing; for screening of blood products; for detection of microbes in bioprocesses, food, water, industrial or environmental samples; or for other purposes. Specific methods, compositions, and kits as disclosed herein provide improved sensitivity, specificity, and/or speed of detection in the amplification-based detection of *Listeria*.

Ribosomal RNA was chosen as the target of the assay since it has high copy number per cell, enabling reliable detection of the targeted pathogen at low cell concentrations (Milner M. G., et al., 2001, *"Relationship between nucleic acid ratios and growth in Listeria monocytogenes,"* Microbiology 147: 2689-2696; Livezey K. et al., 2013, *"A new generation of food-borne pathogen detection based on ribosomal RNA,"* Annu. Rev. Food Sci. Technol. 4: 313-325). Whole genome analysis revealed that a single *L. monocytogenes* cell contains 6 copies of the ribosomal RNA (rrn) operon (Glaser P. et al., 2001, *"Comparative genomics of Listeria species,"* Science 294: 849-852), and expression studies estimated that approximately 600-25,000 copies of the ribosomes were detected per cell. These findings have indicated that targeting rRNA is more than enough for a reliable RT-PCR amplification to enable detection of the targeted pathogen at low cell concentrations. To design oligonucleotides targeting the ribosomal RNA operon (rrn operon), the ribosome sequences of over 200 genomic entries of *Listeria* species were aligned and compared with closely-related bacterial species. Regions in the ribosome sequences were identified that showed the most heterogeneity between the *Listeria* sequences and non-target sequences. Simulated folding was performed to assess RNA accessibility in the identified regions and amplification assays using reverse transcription polymerase chain reaction (RT-PCR) were designed targeting the identified regions in the rrn operon. Standard design criteria for RT-PCR assays were used: the percent GC content of the amplicon primer and probes were close to 50%, the annealing temperature of probes was higher than that of associated primers, and the probes and primers were screened for the possible formation of self-dimers, heterodimers, and hairpins. The selected probes anneal in close proximity to the primer on the same strand, without overlapping the primer sequence. To assess specificity, the results generated with the initial assays were aligned to non-targeted bacterial species, which are commonly found in agricultural environments. Adjustments to the design parameters were made when necessary to ensure the specificity of the assay. Accordingly, the invention relates to methods for detection of *Listeria* in a sample of interest, oligonucleotides, compositions, reactions mixtures, kits, and the like useful for such methods.

U.S. Pat. No. 10,501,812 discloses a transcription-mediated amplification (TMA) method, targeting the 16S rRNA region for identifying *Listeria*. This patent discloses the ability to only identify 7 *Listeria* species, which include *L. monocytogenes, L. innocua, L. welshimeri, L. ivanovii, L. seeligeri, L. grayi*, and *L. murrayi*.

The instant inventors have selected a region that may identify at least 20 species of *Listeria* while still discriminating against closely-related/non-targeted bacterial species. When compared with the assay taught in U.S. Pat. No. 10,501,812, the assay taught herein is ten times more sensitive in detecting *Listeria*.

The aptamers, primers, probes, and methods described herein may be incorporated with an automated system to significantly reduce or eliminate the need for culturing prior to analyzing for the presence of *Listeria*. Consequently, using the methods of the invention the total-time-to-results for foodborne pathogen testing is reduced. With this knowledge, effective intervention strategies can then be implemented to mitigate the presence of these bacterial and viral pathogens in the food supply.

Most methods of pathogen capturing and concentration from large-volume samples will use small micron membrane filters to capture the pathogen. Small particle filtering can be subject to membrane fouling when isolating bacterial pathogens from food and environmental samples, resulting in reduced levels of detection sensitivities. The detection method described herein does not use membrane filtration for pathogen detection, but instead uses an adaptation of depth filtering, a processing stage previously used for preventing filter clogging (Murakami, T., 2012, "Filter-based pathogen enrichment technology for detection of multiple viable foodborne pathogens in 1 day," J. Food Prot. 75: 1603-1610. This method of depth filtering was used in Example 6 where Listeria cells were detected in environmental swab samples. These samples were challenging due to the presence of debris and soil present in the food processing facility. The combinatorial use of depth filtering method in conjunction with the Listeria aptamer capture step proved to be successful in the blind test of Example 6.

Environmental samples may be collected using materials such as those described in the Bacteriological Analytical Manual from the U.S. Food & Drug Administration, available on their web site. For example, samples may be collected with 3M™ Sponge-sticks with Neutralizing buffer (3M, St. Paul, Minn., USA; Catalog #SSL-10NB), which are made out of cellulose; Puritan dry cotton swab (Puritan Medical Supplies, Guilford, Main, USA, Catalog #25-806 1PC, 25-806 2PC), made of cotton; 3M™ Swab-sampler in 10 mL D/E neutralizing broth (3M; Catalog #RS96010DE), made of polyester; World Bioproducts PUR-Blue™ swab sampler (World Bioproducts, Mundelein, Ill., USA, Catalog #BLU-10DE), made of polyurethane. Sample swabs soaked in neutralizing buffer were subsequently blended in 1×PBS at room temperature. The standard ratio for sampling is having the sample to be $\frac{1}{10}^{th}$ the final volume of buffer used (Hitchins, A. D., et al., 2017, "BAM: Detection of Listeria monocytogenes in foods and environmental samples, and enumeration of Listeria monocytogenes in foods, ed. Administration, U.S.D.o.F.a.D).

Aptamers were modified with the spacer sequence for aptamer extension, and were attached to the surface of the capture column [8] by a tether sequence for aptamer surface attachment. The spacer and tether sequences were designed to allow optimal orientation of the aptamer to capture its target, and to enable the aptamers to be released from the column for further downstream processing of the target Listeria cells captured by the aptamer. Collected Listeria cells were mechanically lysed in molecular biology grade water. Extraction of RNA may be performed using any method of RNA extraction known in the art. For example, RNA may be extracted using the RNeasy Protect Mini Kit (Qiagen, Valencia, Calif., USA), or by mechanical lysis to obtain a crude lysate.

A widely used RNA detection method, with numerous modifications, is the quantitative real time polymerase chain reaction (qRT-PCR) technique. Quantitative real time PCR (qRT-PCR) was used in the Examples taught herein. The fluorescein label was on the probe and was activated once released from the probe after annealing with the amplicon as part of the qRT-PCR amplification reaction. The cycling conditions for the RNA-probe based assay are 15 minutes at 54° C., 2 minutes at 95° C., followed by 40 cycles of 3 seconds at 95° C. and 30 seconds at 64° C. The presence of Listeria species was determined by detecting the change in florescence at each cycle of the qRT-PCR reaction. A positive signal was defined as a signal having a CT-value of 35 cycles or lower. Using tenfold serial dilutions of RNA template, a CT-value of 35 cycles was determined to represent the amplification of targeted sequences in 1 cell equivalent.

The food industry typically holds finished product in storage for three days or more while waiting for pathogen test results (Philpott, C, 2009, "A summary profile of pathogen detection technologies," In Food Safety Magazine, Glendale, Calif., USA). Therefore, the development of a method for the rapid detection of foodborne pathogens will dramatically reduce the time needed to systematically identify, isolate, and confirm remediation and resolution of these pathogens. To meet the needs of the food safety industry and regulators on increased sample size and complexity (Kaplan R. M., et al., 2014, "Big data and large sample size: A cautionary note on the potential for bias," J. Clin. Transl. Sci. 7: 342-346; Kuiper H. A. and Paoletti C., 2015, "Food and feed safety assessment: The importance of proper sampling," J. AOAC Int. 98: 252-258), the proposed platform can process larger and more complex samples than currently available tests without a cost penalty. The increased sampling size of the method of the invention will improve the statistical significance of the testing programs and will enable a sampling process that is more accurately representative of the entire agricultural field.

Reducing the time needed for confirmation analysis will greatly reduce the total time-to-results and will enable effective intervention strategies to reduce and mitigate the presence of Listeria. For achieving on-site monitoring of Listeria in processing facilities, the present study developed a method for the effective capturing and concentrating of Listeria cells from environmental swab samples, followed by amplifying the targeted RNA sequences in high copy numbers for Listeria detection. The results presented here indicate that it is possible to conservatively detect less than 5-10 CFU/mL from spiked sponge-swab samples collected at a leafy greens processing facility.

The result of the assay taught herein consists of the classification of the sample as positive or negative for the presence or absence of Listeria. In some embodiments, two or more Listeria species selected from the group consisting of L. monocytogenes, L. innocua, L. welshimeri, L. ivanovii, L. seeligeri, L. grayi, and L. murrayi are amplified. In other preferred embodiments, all of the Listeria species are amplified.

In an embodiment, the sample is for a process stream where Listeria is a known or suspected contaminant. For example, essentially any manufacturing or other process stream that employs one or more samples or sample streams, at least one of which contains living cells, organisms, or components thereof, or contains such cells, organisms or components as a result of unintended contamination, is considered such a process stream. In many such process streams it is desirable to have the ability to detect, identify, and/or control the presence and/or source(s) of living cells, organisms, or components thereof within a process stream. Using the methods disclosed herein, for example, the presence and/or source(s) of Listeria in one or more bioprocess samples and/or streams may be monitored in a rapid and sensitive fashion.

An oligonucleotide can be virtually any length, limited only by its specific function in the amplification reaction or in detecting an amplification product of the amplification reaction. However, in certain embodiments, preferred oligonucleotides will contain at least about 10; or 12; or 14; or 16; or 18; or 20; or 22; or 24; or 26; or 28; or 30; or 32; or 34; or 36; or 38; or 40; or 42; or 44; or 46; or 48; or 50; or 52; or 54; or 56 contiguous bases that are complementary to a region of the targeted nucleic acid sequence or its complementary strand. The contiguous bases are preferably at least about 80%, more preferably at least about 90%, and most preferably completely complementary to the target sequence to which the oligonucleotide binds. The oligonucleotide may contain generally between about 10-100; or 12-75; or 14-50; or 15-40 bases, and optionally can include modified nucleotides.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide. Modifications include base modifications, sugar modifications or backbone modifications. Base modifications are known to those of skill in the art. The nucleoside subunits may be joined by linkages such as phosphodiester linkages, modified linkages or by non-nucleotide moieties which do not prevent hybridization of the oligonucleotide to its complementary target nucleic acid sequence.

The design and sequence of oligonucleotides depend on their function as described below. Several variables to take into account include the length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well-known aspect of oligonucleotide design, and various computer programs are readily available to initially screen large numbers of potential oligonucleotides.

As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent). Probes may have additional nucleosides or nucleobases outside of the targeted region so long as such nucleosides or nucleobases do not substantially affect hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both. A probe is optionally labeled with a fluorescent dye such as the fluorescein molecule, for example, 6-carboxyfluorescein (FAM), an indocarbocyanine illustratively that sells under the tradename QUASAR-670 (LGC Biosearch Technologies; Petaluma, Calif., USA), a hexaflurocine such as 6-carboxyhexafluorescein (HEX), or other fluorophore molecule, and optionally a quencher. A quencher is appreciated to be matched to a fluorophore. Examples of quenchers include the black hole quenchers BHQ1, and BHQ2, and the dihydrocyclo pyrroloindole tripeptide minor groove binder (MGB). Other fluorophores and quenchers are known in the art and are similarly operable herein.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention.

All publications, patents, and patent applications mentioned in this specification are herein incorporated by reference to the same extent as if each individual publication, patent, or patent application was specifically and individually indicated to be incorporated by reference. In addition, the materials, methods, and examples are illustrative only and not intended to be limiting.

Having now generally described this invention, the same will be better understood by reference to certain specific examples, which are included herein only to further illustrate the invention and are not intended to limit the scope of the invention as defined by the claims.

Example 1

Probe Design

Oligonucleotide primers and probes to specifically detect *Listeria* were designed based on *Listeria* ribosomal RNA sequences.

To initiate the design of oligonucleotides, hundreds of genomes of *Listeria* and non-targeted bacterial species were aligned and compared. Regions in the ribosomal sequences with the most heterogeneity between the *Listeria* sequences and non-target sequences were selected for the probe design. Simulated folding was performed to assess RNA accessibility in the identified regions. Probes were designed with a duplex stabilizing technology (Biosearch Technologies, Petaluma, Calif., USA) and are based on standard criteria for RT-PCR assays such as the G-C content, annealing temperatures, and self-hybridization.

To further assess the oligonucleotide specificity for cross hybridization with nontargeted bacterial species from soil, water, and plant surfaces, the in silico mismatch was examined by comparing *Listeria* sequences with *B. cereus*, *Bacillus subtilis* subsp. *spizizenii*, *Enterobacter cloacae*, *Pseudomonas syringae*, and *Citrobacter freundii*.

The designed oligonucleotide probes have the sequences set forth below:

```
SEQ ID NO. 1: Forward primer
5'-CCTTACCAGGTCTTGACATTCTTTG-3';

SEQ ID NO. 2: Reverse primer
5'-GAGCTGACGACAACCATGC-3'

SEQ ID NO. 3: Detection probe:
5'-CACTCTGGAGACAGAGCTTT-3';

SEQ ID NO. 4: Tether sequence
5'-CAACTTTCAAAACAAAAACTTTTTTTTTT-Amino C6-3';

SEQ ID NO. 5: Spacer sequence
5'-GTTTTTGTTTTGAAAGTTGTTTTTTTTTT-3'
```

As seen below, the primers and oligonucleotides described above were used successfully to detect *Listeria* in environmental samples.

Example 2

Assay

This Example describes the assay of the invention. An environmental sample was transferred to a temperature-controlled chamber; bacteria cells were captured using aptamers; captured bacteria were lysed; RNA was prepared from the lysed bacteria; and using the RNA for amplification of the bacteria.

The inventors have developed a method for testing environmental samples for the presence of *Listeria*. A schematic diagram of the sampling, processing steps, and *Listeria* detection methods of the invention are depicted in FIG. 1. Briefly, environmental sample swabs were obtained and blended with phosphate buffered saline (PBS) in filter bag [1]; the blended sample was filtered into sample container [2]; the filtered sample was combined with buffers [3] using pump [4]; and the homogenized material was introduced into a temperature controlled chamber [5]. In the temperature controlled chamber [5]; a microfluidic valve [6] moved the homogenized sample to a depth filter [7] to remove larger particles; the filtered material entered a column [8] where bacterial cells in the sample were captured using aptamers; and potential inhibitors were removed as waste [9]; the captured bacterial cells were mechanically lysed [10] and further collected [11]; and the lysed cells were transferred outside of the temperature controlled chamber [5] to an RNA extraction system [12]. The RNA was then subjected to amplification [13].

Aptamers were modified with the spacer sequence for aptamer extension and were bound to the surface of the capture column [8] by the tether sequence for aptamer surface attachment. FIG. 2A shows the aptamer (set forth in SEQ ID NO: 6; (Suh et al., 2014)) modified with spacer sequence (set forth in SEQ ID NO: 5) for aptamer extension, which is annealing to the tether sequence (set forth in SEQ ID NO: 4) for aptamer surface attachment to the capture column. The tether sequence has an Amino C6 linker at the 3' end to enable surface attachment. The spacer and tether sequences were designed to allow optimal orientation of the aptamer to capture the *Listeria* cells and enable the aptamers to be released from the column for further downstream processing. The aptamer-captured *Listeria* cells were lysed in molecular biology-grade water. After extraction, *Listeria* RNA was amplified and detected with a qRT-PCR reaction using forward primer BH1-F, reverse primer BH1-R, and probe BH1-P. FIG. 2B depicts binding of primer BH1-F (set forth in SEQ ID NO: 1), primer BH1-R (set forth in SEQ ID NO:2), and probe BH1-P (set forth in SEQ ID NO:3) bound to *Listeria* DNA sequence (set forth in SEQ ID NO: 7).

In the present study the sample swabs were collected with 3M™ Sponge-sticks with Neutralizing buffer (3M, Catalog #SSL-10NB), which are made from cellulose. Sample swabs soaked in neutralizing buffer were subsequently blended in 1×PBS at room temperature. The standard ratio for sampling is having the sample to be $\frac{1}{10}^{th}$ the final volume of buffer used. The capture column [8] contained aptamers. The *Listeria* cells were lysed in molecular biology grade water. The cycling conditions for the qRT-PCR assay were 15 minutes at 54° C., 2 minutes at 95° C., followed by 40 cycles of 3 seconds at 95° C., and 30 seconds at 64° C. The presence of *Listeria* species was detected by measuring the change in florescence at each cycle of the qRT-PCR reaction. A positive signal was defined as the one having a CT-value of 35 cycles or lower. This value represents the amplification of the targeted sequences in one cell equivalents, as determined by several experiments using tenfold serial dilutions of RNA template.

The probes listed in Example 1 were used to determine the presence of *Listeria* in samples using the assay taught in Example 2.

Example 3

Assay Specificity

This Example shows that the assay as taught here is specific for *Listeria* determination and has higher sensitivity than the commercially available MicroSEQ® *Listeria monocytogenes* Detection kit (Applied Biosystems, Foster City, Calif., USA).

Side by side assays were performed using the assay of the invention, and the MicroSEQ® *Listeria monocytogenes* Detection kit. The MicroSEQ® *Listeria monocytogenes* Detection kit uses the Polymerase Chain Reaction (PCR) to amplify a unique *Listeria*-specific DNA target sequence and a TaqMan probe to detect the amplified sequence. The kit specifically detects *L. monocytogenes* serotypes: 1/2A, 1/2B, 1/2C, 3A, 3B, 3C, 4A, 4AB, 4B, 4C, 4D, 4E, and 7. The kit does not detect other pathogens. Reactions containing *L. monocytogenes* cell lysate template were tested.

*L. monocytogenes* strain RM2199 was incubated overnight at 37° C. on tryptic soy yeast agar (TSYEA, Difco, Detroit, Mich., USA). A 1 µL loop of culture was inoculated in 5 mL Luria-Bertani (LB) broth (Difco) and incubated at 37° C. with shaking at 200 rpm to mid-log phase ($OD_{600}$ 0.2-0.3). A 2 mL aliquot of the culture was removed and pelleted by centrifugation. The supernatant was discarded, and the pellet was resuspended in 2 mL 1× phosphate-buffered saline (PBS) buffer and centrifuged again. The supernatant was removed, and the pellet was resuspended in 2 mL nuclease-free water. Ten-fold dilutions were made and 200 µL of each dilution were lysed using an OmniLyse® device (Claremont BioSolutions LLC, Upland, Calif., USA). The cell count of each dilution was confirmed by plate enumeration. The final aliquots of lysed cells were made with concentrations of 1 cell; 100 cells; and 1000 cells per microliter. PCR amplifications using the MicroSEQ® *Listeria monocytogenes* Detection kit consisted of a 30 µL reaction mixture containing 5 µL of lysed template. The cycling conditions were 2 minutes at 95° C., followed by 40 cycles of 3 seconds at 95° C., and 30 seconds at 60° C. RT-qPCR amplifications consisted of a 20 µL reaction mixture, each containing 5 µL of lysed template, 0.5 µM of each forward and reverse primers, 0.1 µM of the BHQplus® probe (Biosearch Technologies, Petaluma, Calif., USA), and 1× TaqPath™ 1-Step Multiplex Master Mix (Applied Biosystems, Foster City, Calif., USA). The cycling conditions were 15 minutes at 54° C., 2 minutes at 95° C., followed by 40 cycles of 3 seconds at 95° C., and 30 seconds at 64° C. Both reaction mixtures were placed in a QuantStudio 5 Real-Time PCR System (Applied Biosystems).

BHQplus® probe with DNA duplex stabilizing technology were used in place of the conventional TaqMan® probe (Roche Molecular Systems, Pleasanton, Calif., USA). The BHQplus® probe technology was selected since the nucleotide base analogs promoting duplex stabilizing effect (Kutyavin I. V., 2008, *"Use of base-modified duplex-stabilizing deoxynucleoside 5'-triphosphates to enhance the hybridization properties of primers and probes in detection polymerase chain reaction,"* Biochemistry 47: 13666-13673), enabling higher annealing temperatures and thus greater specificity when compared to the TaqMan® probes. The results are shown in FIG. 3. The estimated amounts of template per reaction were 5,000 (circles), 500 (triangles), 50 (diamonds) cells, and 5 (squares) cells. The RNA-based assay of the instant invention (filled symbols) was found to be 100-times more sensitive than the DNA-based commercial kit (open symbols).

Example 4

Assay Sensitivity

The assay of the invention is specific for *L. monocytogenes*, even in the presence of excess non-target RNA.

The specificity of the assay of the invention was tested in the presence of either 100 fg of *L. monocytogenes* RNA, or 20 ng of non-target RNA (excess), which was equivalent to approximately 2 million non-target cells and 4 billion copies of non-target RNA sequences (Milner M. G., et al., 2001, "Relationship between nucleic acid ratios and growth in *Listeria monocytogenes*," Microbiology 147: 2689-2696). The non-target RNA was extracted from environmental gram-positive bacterial strains, *B. cereus* and *B. subtilis* subsp. *spizizenii*, which are closely related to *L. monocytogenes* as well as gram-negative environmental bacterial strains, *C. freundii*, *E. cloacae*, and *P. syringae*.

*L. monocytogenes* strain RM2199 was streaked from frozen stock culture on TSYEA (Difco) at 37° C. overnight. *B. cereus* strain ATCC 14579 was streaked from a frozen stock culture on nutrient agar (Difco) at 28° C. overnight. Each bacterial strain was inoculated in 1×PBS buffer to $OD_{600}$ 0.2-0.3. Total RNA was extracted and purified using the RNeasy® Protect Mini kit (Qiagen, Valencia, Calif., USA) according to the manufacturer's protocol. RNA quality was assessed using the RNA 6000 Nano kit with the 2100 Bioanalyzer instrument (Agilent Technologies, Santa Clara, Calif., USA). The RNA was diluted to 100 fg per microliter for *L. monocytogenes* and 100 fg, 1 pg, 10 pg, and 100 pg per microliter for *B. cereus*. RT-qPCR amplifications consisted of a 20 µL reaction mixture, each containing 1-2 µL of the of purified RNA depending on the combination of templates tested, 0.5 µM of each forward and reverse primer, BH1-F and BH1-R (Biosearch Technologies), 0.1 µM of the BH1-P, BHQplus® probe (Biosearch Technologies), and 1×TaqPath™ 1-Step Multiplex Master Mix (Applied Biosystems). The reaction mixtures were placed in a QuantStudio 5 Real-Time PCR System (Applied Biosystems) and the cycling conditions were 15 minutes at 54° C., 2 minutes at 95° C., followed by 40 cycles of 3 seconds at 95° C., and 30 seconds at 64° C.

The data obtained is shown in Table 2, below.

TABLE 2

| | Sample | Tested Strain | Source | Signal |
|---|---|---|---|---|
| Gram Positive Bacteria | *Listeria monocytogenes* | RM2199 | Human | Positive |
| | *Bacillus cereus* | ATCC 14579 | Soil | Negative |
| | | RM5142 (6A2) | Soil | Negative |
| | | RM5143 (6A3) | Soil | Negative |
| | *Bacillus subtilis* subsp. *spizizenii* | ATCC 6633 | Soil | Negative |
| Gram Negative Bacteria | *Citrobacter freundii* | RM4680 | Lettuce | Negative |
| | *Enterobacter cloacae* | RM9194 | Spinach | Negative |
| | *Pseudomonas syringae* | RM1952 (B728a) | Bean | Negative |
| | Negative | Control | N/A | Negative |

High fluorescent signals were recorded when examining the clinical *L. monocytogenes* strain RM2199 or the plant-associated *L. grayi* strain RM2208 while no signal amplification was detected for any of the tested non-target strains when using the probe-based assay. As seen in Table 2 and in FIG. 4, the only positive signal was obtained from *Listeria* species, *L. monocytogenes* or *L. grayi*. The dashed line in FIG. 4 indicates the detection threshold limit of the assay. No amplification (CT value) was detected for the non-target strains tested.

The assay of the invention detected *L. monocytogenes*, even in the presence of excess RNA from the non-target *B. cereus*. Low amounts (100 fg) of *L. monocytogenes* RNA in the presence of various amounts (100 fg, 10 pg, or 100 pg) of *B. cereus* strain ATCC 14579 were co-amplified using the assay taught here. The results are shown in FIG. 5.

As seen in FIG. 5, no significant differences in the measured Ct-values were observed. To examine the effect of various amounts of *Bacillus* RNA on the efficiency of the amplification of the *Listeria* sequences, the slope of the curve at the pre-inflection point was examined. Analysis of the amplification curve resulted in no significant change in the slope of the curve under the various conditions tested, demonstrating that the efficiency of the amplification may not be adversely affected by addition of the non-target template.

Example 5

Increased Detection Sensitivity

Detection sensitivity of the assay taught herein was directly correlated to the mechanical lysis procedure used.

The assay sensitivity was tested using 16-fold serial dilutions of samples starting with a sample containing over an estimated 1,000,000 cells of *L. grayi*. The samples were subjected to an ultrasonic cell disruption procedure for efficient cell lysis. The lysis was followed by nucleic acid extraction without column purification. The cell concentration of *Listeria* cells, used as starting material for this experiment, was determined by measuring optical density and plate enumeration on solid medium for estimating the *Listeria* cell concentration amounts.

The data is presented in FIG. 6. As expected, this figure shows that the results from the negative control are below the detection threshold limit. The figure also shows that the Ct-values of the serial dilutions were about 4 cycles apart indicating close to 100% efficiency in the amplification of the target sequence. Filled circles present data for sample with *Listeria* 100 times above infectious dose; filled diamonds present data for sample with *Listeria* 10 times above infectious dose; filled triangles present data for *Listeria* at infectious dose; filled squares present data for *Listeria* 15 times below infectious dose; negative control grey line has no additional symbols.

Example 6

*Listeria* Detection in Environmental Samples

The aptamer-based capture test accurately detected *Listeria* species in a blind test of environmental swab samples, some of which were spiked with *L. grayi*.

Environmental swab samples, collected using stick-mounted sponges, were obtained from distinct locations at a leafy greens processing facility. The samples were selected from distinct locations considered representative of the processing facility and challenging due to the presence of inhibitors of detection assays. Each sponge was processed as described in FIG. 1. Some of the environmental samples were spiked with 3.5 CFU/mL to 1000 CFU/mL *L. grayi* in a blinded fashion.

As shown in FIG. 7, the assay of the invention accurately detected *Listeria* in all spiked samples (open symbols). No positive signal was recorded in any of the samples that were not spiked (filled symbols), indicating that the assay did not report false positive or false negative results. The amount of bacteria detected in these unspiked samples was lower than 1 CFU/mL and at cell concentrations below the threshold limit of detection of the assay.

We claim:

1. A *Listeria monocytogenes* detection kit comprising a forward oligonucleotide primer with a nucleotide sequence of SEQ ID NO: 1 and a reverse oligonucleotide primer with a nucleotide sequence of SEQ ID NO: 2 that bind to at least one *Listeria* spp. polynucleotide, a probe oligonucleotide that specifically binds to a *Listeria monocytogenes* polynucleotide; wherein the probe contains a fluorophore at the 5' end and a quencher at the 3' end, and has the nucleotide sequence of SEQ ID NO: 3; an aptamer oligonucleotide with a nucleotide sequence of SEQ ID NO: 6, a spacer for aptamer extension oligonucleotide with a nucleotide sequence of SEQ ID NO: 5, and a tether oligonucleotide for aptamer surface attachment with a nucleotide sequence of SEQ ID NO: 4.

2. The *Listeria monocytogenes* detection kit of claim 1, further comprising polynucleotide-amplification reagents.

3. A method for detecting *Listeria monocytogenes* in a sample, the method comprising:
   capturing bacterial cells in the sample by using at least one aptamer with a nucleotide sequence of SEQ ID NO: 6, a spacer for aptamer extension oligonucleotide with a nucleotide sequence of SEQ ID NO: 5, and a tether oligonucleotide for aptamer surface attachment with a nucleotide sequence of SEQ ID NO: 4;
   lysing the captured bacterial cells; and
   amplifying bacterial polynucleotides from the lysed bacterial cells using an oligonucleotide forward primer with a nucleotide sequence of SEQ ID NO: 1, an oligonucleotide reverse primer with a nucleotide sequence of SEQ ID NO: 2, and a probe;
   wherein the probe contains a fluorophore at the 5' end and a quencher at the 3' end, and has the nucleotide sequence of SEQ ID NO: 3; and
   wherein the presence of amplified polynucleotides is an indication that *Listeria monocytogenes* is present in the sample.

4. The method of claim 3, wherein at least one of the capturing and the lysing of the bacterial cells is performed inside a temperature-controlled chamber.

5. The method of claim 4, wherein both, the capturing and the lysing of the bacterial cells is performed inside a temperature-controlled chamber.

6. The method of claim 3, wherein the bacterial polynucleotides are RNA.

7. The method of claim 3, wherein the bacterial polynucleotides are amplified using quantitative reverse transcription polymerase chain reaction (qRT-PCR).

8. The method of claim 3, wherein the sample is an environmental sample.

9. The method of claim 3, wherein *Listeria monocytogenes* is detected in the sample without an enrichment culturing step.

* * * * *

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Synthetic Forward Primer

<400> SEQUENCE: 1
ccttaccagg tcttgacatt ctttg                                              25

<210> SEQ ID NO 2
<211> LENGTH: 19
<212> TYPE: DNA
<213> ORGANISM: Artificial Sequence
<220> FEATURE:
<223> OTHER INFORMATION: Synthetic Reverse Primer

<400> SEQUENCE: 2
gagctgacga caaccatgc                                                     19

<210> SEQ ID NO 3
<211> LENGTH: 20
<212> TYPE: DNA
<213> ORGANISM: Artificial Sequence
<220> FEATURE:
<223> OTHER INFORMATION: Synthetic Detection Probe

<400> SEQUENCE: 3
cactctggag acagagcttt                                                    20

<210> SEQ ID NO 4
<211> LENGTH: 29
<212> TYPE: DNA
<213> ORGANISM: Artificial Sequence
<220> FEATURE:
<223> OTHER INFORMATION: Synthetic tether sequence

<400> SEQUENCE: 4
caactttcaa aacaaaaact tttttttt                                           29

<210> SEQ ID NO 5
<211> LENGTH: 29
<212> TYPE: DNA
<213> ORGANISM: Artificial Sequence
<220> FEATURE:
<223> OTHER INFORMATION: Synthetic Spacer Sequence

<400> SEQUENCE: 5 gttttgttt tgaaagttgt tttttttt                                            29

<210> SEQ ID NO 6
<211> LENGTH: 81
<212> TYPE: DNA
<213> ORGANISM: Artificial Sequence
<220> FEATURE:
<223> OTHER INFORMATION: Synthetic Aptamer
```

```
<400> SEQUENCE: 6
agtatacgta ttacctgcag ctctgtgttc cgttttcgat tcttactgtg ttttcgggtg        60
ccgatatctc ggagatcttg c                                                  81

<210> SEQ ID NO 7
<211> LENGTH: 93
<212> TYPE: DNA
<213> ORGANISM: Listeria monocytogenes

<400> SEQUENCE: 7
ccttaccagg tcttgacatc ctttgaccac tctggagaca gagctttccc ttcggggaca        60
aagtgacagg tggtgcatgg ttgtcgtcag ctc                                     93
```